United States Patent [19]

Hershberger

[11] Patent Number: 4,806,474

[45] Date of Patent: Feb. 21, 1989

[54] PREPARATION OF MYCELIAL CHITOSAN AND GLUCAN FRACTIONS FROM MICROBIAL BIOMASS

[75] Inventor: Donald F. Hershberger, Elkhart, Ind.

[73] Assignee: Miles Inc., Elkhart, Ind.

[21] Appl. No.: 743,108

[22] Filed: Jun. 10, 1985

[51] Int. Cl.[4] ............... C12P 19/04; C12P 1/02; C12R 1/685; C08B 37/08

[52] U.S. Cl. .................... 435/101; 435/171; 435/917; 536/20

[58] Field of Search ............. 435/101; 536/20

[56] References Cited

U.S. PATENT DOCUMENTS 4,195,175  3/1980  Peniston et al. ............... 536/20
4,282,351  8/1981  Muzzarelli ..................... 536/20

FOREIGN PATENT DOCUMENTS 2923802  6/1979  Fed. Rep. of Germany .

OTHER PUBLICATIONS

Stagg, C. M., et al., (1973), Biochem. Biophys. Acta, 320, 64–72.

Sielsma, J. H., et al., (1986)in: *Chitin in Nature and Technology*, Plenum Press (Muzzarelli et al., eds), pp. 63–69.

Biotechnology and Bioengineering, vol. XXII, pp. 885–896, (1980).

*Primary Examiner*—Thomas G. Wiseman
*Assistant Examiner*—Charles L. Patterson, Jr.
*Attorney, Agent, or Firm*—Jerome L. Jeffers

[57] ABSTRACT

Chitin from microbial biomass is converted to chitosan and recovered as an essentially glucan-free product. The method involves contacting the biomass with a strong alkali solution at a temperature within the range of from 60° to 90° C. for a period of at least 10 hours to form an insoluble chitosan/glucan residue. The chitosan is then recovered by adding dilute acid to the residue to dissolve it without dissolving the glucan which can then be recovered separately.

9 Claims, No Drawings

PREPARATION OF MYCELIAL CHITOSAN AND GLUCAN FRACTIONS FROM MICROBIAL BIOMASS

BACKGROUND OF THE INVENTION

Chitosan, a natural polysaccharide, is commercially important because of its properties as a natural polycationic polymer which is soluble in dilute acid. It has many uses as a flocculant or precipitation agent and is also used as a cross linkable matrix for immobilization of enzymes or microbial cells. Many other uses are suggested from its film forming properties and its polyelectrolyte behavior. Chitin, the precursor of chitosan is available, for example, in the shells of crustaceans from which it can be isolated after extracting the shells with acid and alkali to remove mineral matter and protein components.

The byproducts of fermentation processes such as the biomass recovered after the controlled fermentation of fungi, molds and yeasts contain chitin together with other biopolymers such as glucan. Muzzarelli discloses in German Patent Publication DE-05 No. 2,923,802 a method for obtaining a chitosan-glucan complex by treating the mycelia of hyphomycetes such as those from the genus Aspergillus with a strong, concentrated alkali at a temperature near the boiling point of the solution to solubilize the mycelial material other than a resulting chitosan-glucan complex and then recovering this insoluble material. This patent discloses a typical procedure in which the biomass is treated with a 30-50% sodium hydroxide solution at its boiling temperature (118°-130° C.) for 4-6 hours. The author states that at a lower temperature, shorter times of treatment and lower sodium hydroxide concentrations, glucan is solubilized and removed less effectively and there is only limited deacetylation of the chitin to form chitosan. This would be inimical to his stated goal of forming a chitosan-glucan complex which is capable of collecting and binding manganese ions.

Muzzarelli, Tanfani and Scarpini report in *Biotechnology and Bioengineering*, Vol. XXII, pp. 885-896 (1980) that waste mycelia of Aspergillus niger from citric acid production can be treated with boiling 30-40% NaOH aqueous solutions for 4-6 hours to obtain an insoluble chitosan-glucan complex.

SUMMARY OF THE INVENTION

The present invention is a method for recovering chitosan from chitin containing biomass which comprises the steps of:

(a) contacting the biomass with a concentrated aqueous solution of a strong alkali wherein the amount of alkali is from 200% to 500% of the amount of biomass on a dry weight basis;

(b) maintaining the biomass in contact with the alkali solution for a period of at least 10 hours while maintaining the mixture's temperature in the range of from 60° C. to 90° C. to convert the chitin in the biomass to chitosan;

(c) separating the chitosan from the alkali solution and washing it; and (d) recovering the chitosan from undissolved residue from step c by dissolution in dilute acid.

DESCRIPTION OF THE INVENTION

Chitin containing biomass suitable for use in the present invention can be obtained by the culturing of various species of fungi such as those from the genera Mucor, Aspergillus, Streptomyces, Phycomyces, Choanephora, Saccharomyces and Basidiomyces. The resulting biomass contains chitin linked to glucan in the structure of the cell walls. It is convenient when such cultures are used for the production of products such as antibiotics, organic acids or alcohols with the concomitant formation of waste biomass containing considerable proportions of chitin to use this waste biomass as a source of chitosan obtainable by alkali treatment.

In the examples which follow, the experimentation was carried out using the waste biomass from a submerged fermentation of a strain of *Aspergillus niger* which is used to produce citric acid from substrates such as sucrose or glucose. Upon completion of a batch fermentation, the white biomass consisting of spherical aggregates of hyphal material is filtered from the broth using a vacuum cloth belt filter upon which it is washed with a small amount of warm water to displace residual broth and is dewatered to a level of approximately 25% dry solids content. Of the dry solids obtainable from the biomass, about 20% to 25% is estimated to be chitin.

The biomass, having a water content of from 70% to 80% (w/w) is then contacted with a concentrated aqueous solution of a strong alkali. Suitable alkalis include NaOH, LiOH and KOH; NaOH is preferred. The amount of alkali used should be at least 200% of the biomass being treated up to about 500% on a dry weight basis in order to accomplish the goals of this invention. By a concentrated solution it is intended that the alkali should be at least 40 weight percent in terms of its content in the aqueous phase of the solution. This is the case because hydrolysis reaction rates are affected by alkali concentration, water activity and heat while deacetylation is affected by alkali concentration and heat. The water content and heat are kept at restricted levels to minimize hydrolysis reactions relative to deacetylation resulting in less polymer degradation of both glucan and chitin initially present in the biomass. Deacetylation of the chitin under the specified conditions is sufficient, however, to give a deacetylated chitin fraction (chitosan) which is soluble in dilute acid.

After contact of the biomass with the concentrated alkali solution, they are maintained in contact for a period of at least 10 hours while maintaining the temperature at a level of from 60° to 90° C. Preferably, the reaction is carried out at a temperature of from 75° to 85° C. for a period of from 16 to 24 hours. This procedure converts the chitin in the biomass to chitosan and also hydrolyzes linkages to the associated glucan.

It has been discovered that the chitosan and glucan can be separated from each other after separating their residues from the alkali soluble components of the biomass. This is accomplished by washing the residues by repeated slurrying in water followed by centrifugation and decantation. The washed residues are then extracted with a weakly acidic rinse such as by the addition of acetic, formic, citric, or hydrochloric acid in sufficient quantity to lower the pH to the level of from 3 to 5. This leaves a residue of acid insoluble glucan which can be separated from the acidic chitosan solution by liquid/solid separatory techniques. This results in the formation of a dilute acid solution of chitosan containing only small amounts (less than 155 by weight) of glucan. The acid insoluble residue which is left is a highly hydrated glucan relatively free of associated chitin or chitosan. These two resultant materials are utilized for different purposes. For example, the glucan may be utilized for its water binding capacity as a bulking agent, moisture absorbent, viscosifier, lubricant, paste stabilizer or similar agent. It also contains some fibrous nature which renders it useful as a paper additive, absorbent, or similar agent. The mycelial chitosan can be used in a manner similar to shellfish chitosan, such as, for example, a polycationic flocculant, a film former, a cross-linkable matrix for enzyme and microbe immobilization, a complexing agent for metals/iodine/-fatty acids or as a deacidulant.

The advantages of the present method vis-a-vis the prior art are that:

1. Sodium hydroxide usage is reduced to a minimum. In spite of the fact that a high concentration of alkali is required, it is used either as a solid which is mixed into the dump mycelium to a thick paste consistancy or as a concentrated solution in water with evaporation of the mixture under vacuum to obtain a greater than 40% concentration in the total aqueous phase present to provide a thick paste.

2. The process results in less degradation of both the chitosan and the glucan recovered and gives separate resultants of each material which can be used for different purposes.

3. Glucan is recoverable in greater yield than in the prior art process.

4. The chitosan recovered is of higher molecular weight as indicated by its solution viscosity and retention during dialysis.

5. The strength of films formed by drying the acid solution of chitosan obtained by the present process is much greater than that obtained by the prior art process. This is desirable because the effectiveness of the chitosan as a flocculant for many applications or as a cross-linkable matrix depends on its molecular weight.

6. The present chitosan is colorless which renders it particularly suitable for applications related to food uses.

7. Since more free glucan is obtained, less is degraded and left in the spent sodium hydroxide solution thereby rendering the alkali more suitable for recycle.

While the present invention is not predicated upon any particular theory of operation, it is believed that the superior results observed during the use of this method are obtained due to minimizing hydrolysis relative to deacetylation reactions by keeping the temperature no greater than 90° C. and water content of the alkali solution below 60%.

The method of practicing the present invention is further illustrated by the following examples.

EXAMPLE I

Damp mycelia from a deep fermentation of an organism from the species *Aspergillus niger* containing approximately 75% water was obtained as a belt filter cake from the filtration used to remove the waste biomass from a commercial fermentation for the production of citric acid using the organism. This procedure has been described in more detail above. To a 400g portion of this material was added 400g of a 50% (w/w) aqueous sodium hydroxide and 240g of sodium hydroxide pellets to provide an overall aqueous sodium hydroxide concentration of approximately 46.8% (w/w). After mixing the resultant to a homogeneous mass, it was covered and incubated at about 80° C. for 18 hours in an oven. The resultant mix was washed by repeated dilution with water to about 2400 ml followed by centrifugation until the residual alkali was reduced to less than 0.025 N concentration.

This residue was then slurried with water to about 2.5 liter whereupon acetic acid was added with mixing to bring the pH to 3.8. This mix was centrifuged and the supernate reserved as the first extract. The residue was again mixed with water to about 2.5 liter whereupon acetic acid was added with mixing to bring the pH to 3.8. This mix was centrifuged and the supernate reserved as the second extract. The residue was again mixed with water and acetic acid to pH 3.8 and centrifuged. The two dilute extracts were combined and adjusted to a pH of about 10 by the addition of sodium hydroxide solution thereby precipitating extracted chitosan which was recovered by centrifugation with decantation, washed once with water and dissolved in the first extract with stirring. The resulting 2320 ml solution contained 0.6 g/dl chitosan as estimated by dried film weight less carbohydrate content (estimated as glucose equivalent determined by phenol-sulfuric acid test) less 30% estimated acetic acid content associated with the chitosan. The extraneous carbohydrate content (including glucan) recovered with the chitosan equaled an additional 7% by weight. Based on this, it was calculated that the recovery of chitosan from the initial dry mycelia was 14% (w/w).

EXAMPLE II

This example describes a series of experiments in which a comparison was made between the conditions of alkali treatment used in the present invention and those described in the prior art method of Muzzarelli.

Two 400g portions of fresh damp mycelia were mixed with 200g NaOH pellets each. The resulting mixtures, representing 40% w/w aqueous NaOH concentration, were incubated for 5 hours at 125° to 130° C. in covered containers. These conditions represent those recommended by Muzzarelli and the runs were designated A and B.

Two more 400g portions of the same batch of fresh mycelia (25% mycelia on a dry basis as in the previous runs) were mixed with 240g and 280g, respectively, of NaOH solid pellets and designated C and D. When well mixed, these were incubated at 80° C. for 20 hours.

Samples A, B, C and D were recovered in the manner described in Example I and comparisons of both their chemical and physical properties made. These comparisons are set out in Table I.

TABLE I

|  | A | B | C | D |
|---|---|---|---|---|
| Chitosan (dilute acetic acid extract | | | | |
| Total dried solids/g | 21.9 | 22.1 | 17.2 | 16.2 |
| % carbohydrate (non chitosan/chitin)[1] | 3.2 | 3.1 | 4.8 | 4.9 |
| Total chitosan, g[2] | 14.0 | 14.3 | 10.5 | 9.9 |
| Percent of initial weight | 14.0 | 14.3 | 10.5 | 9.9 |
| Color | pale amber | pale amber | nil | nil |
| Film strength[3] | nil | nil | strong | strong |
| Amine titration[4] meq/g | 4.79 | 4.69 | 4.35 | 4.37 |
| Percent deacetylation[5] | 80.9 | 79.5 | 74.7 | 74.9 |
| Viscosity of 0.49% Chitosan solution, pH 4 (25° C., centistokes)[6] | 2.61 | 2.67 | 4.45 | 4.41 |
| Percent retained[7] | 73.6 | N/D* | 99.2 | *N/D |

TABLE I-continued

|  | A | B | C | D |
|---|---|---|---|---|
| on dialysis |  |  |  |  |
| Total N assay, μg/mg chitosan[8] | 84 | 82 | 83 | 82 |
| Glucan (residue) |  |  |  |  |
| Total dried solids, g | 22.2 | 21.0 | 31.7 | 31.7 |
| Percent of initial weight | 22.2 | 21.0 | 31.7 | 31.7 |
| Percent volatiles[9] | 95.6 | 96.15 | 96.4 | 96.5 |
| Hydration factor[10] | 21.7X | 25X | 26X | 27.6X |
| Color | pale amber | pale amber | nil | nil |

*N/D = not determined
[1]Determined by phenol/sulfuric acid test results expressed as glucose equivalent.
[2]Total chitosan = [dried solids − sodium acetate] (determined by measurement of the acetic acid needed to neutralize the washed residue) − carbohydrate] − 30% estimated acetic acid associated with the chitosan in similar dried film determination.
[3]Film strength determined by pulling the film apart by hand.
[4]Amine titration was determined on chitosan which was precipitated from water solution at pH 10 followed by water washing to remove residual alkali and sodium acetate. The washed chitosan was slurried in water and titrated to a stable pH of 3.5 using 0.1 N HCl and correcting by a value for blank titration of the water used to the same pH. The results were expressed as milliequivalents per gram of assumed chitosan.
[5]The percent deacetylation is calculated as follows:

$$\% \text{ deacetylation} = \frac{100 \times 203}{42 + \text{apparent molecular wt.}}$$

where apparent molecular wt. is the inverse of the amine titration expressed as mg/meq.
[6]The viscosity was determined using a Cannon-Fenske type viscometer on both solutions diluted to the same polymeric solids concentration.
[7]The recovery from dialysis was obtained by comparison of the dry substance film weight of solutions after dialysis with the calculated chitosan contents going into dialysis.
[8]Kjeldahl analysis of N (Chitin contains 6.9% N while chitosan contains 8.7% N.)
[9]Percent volatiles determined by thin film at 45° C. in fume hood.
[10]Hydration factor determined by dividing the weight loss of drying the supernate-free centrifuged paste by the final dry weight.

From Table I it can be determined that, while total chitosan recovery was lower in runs C and D, it was of better quality as indicated by less color, greater film strength, greater viscosity and greater retention by dialysis. All of these indications result from less degradation of the chitosan molecules during the alkali treatment resulting in a product having a higher molecular weight. The essentially equal nitrogen assays of each sample established that the comparisons were made on the basis of equal amounts of chitosan in each sample tested.

It can also be determined from Table 1 that the recovery of undissolved glucan obtained by the present process was 47% greater than that obtained using the prior art process. The recovered glucan also exhibited less undesired color and greater desirable hydration. Since more glucan was recovered, less became solubilized in the spent alkali. This reduces the waste load associated with the spent alkali and makes tentative recycle of part of the alkali more feasible.

What is claimed is:

1. A method for recovering chitosan from chitin containing biomass which comprises the steps of:
   (a) contacting damp biomass with a concentrated aqueous solution of a strong alkali wherein the amount of alkali is from 200% to 500% of the amount of biomass on a dry weight basis;
   (b) maintaining the biomass in contact with the alkali solution for a period of at least 10 hours while maintaining the mixture's temperature in the range of from 60° to 90° C. to convert the chitin in the biomass to chitosan;
   (c) separating the chitosan from the alkali solution and washing it; and
   (d) recovering the chitosan from undissolved residue from step c by dissolution in dilute acid.

2. The method of claim 1 wherein the alkali is NaOH, LiOH or KOH.

3. The method of claim 2 wherein the alkali is NaOH.

4. The method of claim 1 wherein the alkali is at least 40% in terms of its content in the aqueous phase of the solution.

5. The method of claim 1 wherein the biomass is maintained in contact with the alkali solution for a period of from 16 to 24 hours at a temperature of from 75° to 85° C.

6. The method of claim 1 wherein the residue is placed in dilute acid solution by the addition of acetic, formic, citric or hydrochloric acid in sufficient quantity to lower the pH to a level within the range of 3 to 5.

7. The method of claim 1 wherein the biomass is recovered from the fermentation of an organism from the species Aspergillus niger.

8. The method of claim 1 wherein the chitosan is recovered from the dilute acid solution thereof formed in step d by adding base to the solution in sufficient amount to precipitate the chitosan.

9. A method for the recovery of chitosan from chitin containing biomass produced by the deep fermentation of an organism of the species Aspergillus niger which fermentation process provides damp biomass upon filtration and which method comprises the steps of:
   (a) contacting the damp biomass with an aqueous solution of NaOH containing at least 40 weight percent NaOH in terms of its content in the aqueous phase of the solution wherein sufficient solution is used to provide an amount of NaOH of from 200% to 500% of the amount of biomass on a dry weight basis;
   (b) maintaining the biomass in contact with the NaOH solution for a period of time of from 16 to 24 hours while maintaining the temperature in the range of from 7520 C. to 85° C. to convert the chitin in the biomass to chitosan;
   (c) separating the chitosan from the NaOH solution by repeated slurrying in water followed by centrifugation and decantation to recover a washed undissolved residue containing chitosan and glucan;
   (d) recovering the chitosan from the washed residue by the addition thereto of sufficient acid to lower the pH to a lever of from 3 to 5 to solubilize the chitosan without solubilizing the glucan; and
   (e) separating the solubilized chitosan from the insoluble glucan by liquid/solid separatory techniques.

* * * * *